United States Patent
Fujii et al.

(10) Patent No.: US 8,462,995 B2
(45) Date of Patent: Jun. 11, 2013

(54) METHOD OF AUTHENTICATING INDIVIDUAL AND APPARATUS OF AUTHENTICATING INDIVIDUAL USED FOR THE SAME

(75) Inventors: Hitoshi Fujii, Kitakyushu (JP); Kenji Okamoto, Iizuka (JP)

(73) Assignees: Kyushu Institute of Technology, Kitakyushu-shi (JP); Syscom Japan, Inc., Kitakyushu-shi (JP)

(*) Notice: Subject to any disclaimer, the term of this patent is extended or adjusted under 35 U.S.C. 154(b) by 246 days.

(21) Appl. No.: 12/936,469

(22) PCT Filed: Mar. 31, 2009

(86) PCT No.: PCT/JP2009/056595
§ 371 (c)(1),
(2), (4) Date: Oct. 5, 2010

(87) PCT Pub. No.: WO2009/125689
PCT Pub. Date: Oct. 15, 2009

(65) Prior Publication Data
US 2011/0033091 A1 Feb. 10, 2011

(30) Foreign Application Priority Data
Apr. 6, 2008 (JP) ................................. 2008-098820

(51) Int. Cl.
*G06K 9/62* (2006.01)
(52) U.S. Cl.
USPC ........................................................ 382/117
(58) Field of Classification Search
None
See application file for complete search history.

(56) References Cited

U.S. PATENT DOCUMENTS

| | | | |
|---|---|---|---|
| 6,393,139 B1 | 5/2002 | Lin et al. | |
| 8,184,867 B2* | 5/2012 | Otto et al. | 382/117 |
| 2003/0152252 A1 | 8/2003 | Kondo et al. | |
| 2004/0127778 A1* | 7/2004 | Lambert et al. | 600/318 |
| 2009/0202113 A1* | 8/2009 | Fujii et al. | 382/117 |

FOREIGN PATENT DOCUMENTS

| | | |
|---|---|---|
| CN | 1437161 A | 8/2003 |
| JP | 04-242628 | 8/1992 |
| JP | 05-073666 | 3/1993 |
| JP | 5-28133 | 4/1993 |
| JP | 5-28134 | 4/1993 |
| JP | 07-213511 | 8/1995 |
| JP | 08-016752 | 1/1996 |

(Continued)

*Primary Examiner* — Brian P Werner
(74) *Attorney, Agent, or Firm* — McGlew and Tuttle, P.C.

(57) ABSTRACT

Individual authentication method and apparatus therefor, wherein at least one information out of an eyeground blood vessel image information obtained by an optical means, eyeground blood flow distribution image information obtained by using a laser, and information relating to the change over time thereof is compared and collated with personal information registered in advance, and at least the one information out of the eyeground blood vessel image information, the eyeground blood flow distribution image information, and the information relating to the change over time thereof within a measurement field of view obtained in a direction of a line of sight fixed by a fixation target registered in advance is compared and collated with the personal information registered in advance. The fixation target for fixing the direction of the line of sight may be selected from a plurality of fixation points, such as a part of a character string, a part of a still image, or a part of a moving picture, and has an information of which of them to fixedly view registered in advance. An improved technology for further reinforcing the individual authentication method using measurement of an eyeground blood vessel pattern or an eyeground blood flow distribution is provided.

12 Claims, 3 Drawing Sheets

FOREIGN PATENT DOCUMENTS

| | | |
|---|---|---|
| JP | 08-112262 | 5/1996 |
| JP | 11-149453 | 6/1999 |
| JP | 11-215119 | 8/1999 |
| JP | 2001-137191 | 5/2001 |
| JP | 2001-215109 | 8/2001 |
| JP | 2003-164431 | 6/2003 |
| JP | 2003-180641 | 7/2003 |
| JP | 2003-331268 | 11/2003 |
| JP | 2004-046451 | 2/2004 |
| JP | WO 2005/122896 | 12/2005 |
| JP | 2007-041831 | 2/2007 |
| JP | WO 2007/097129 | 8/2007 |
| JP | WO 2007/142055 | 12/2007 |
| WO | WO 2007017207 A1 * | 2/2007 |
| WO | WO 2007142055 A1 * | 12/2007 |

* cited by examiner

FIG. 4

```
2008/3/11 Tue 19:27:31

0  1  2  3
    4  5  6  7
    8  9  A  B
    C  D  E  F
```

METHOD OF AUTHENTICATING INDIVIDUAL AND APPARATUS OF AUTHENTICATING INDIVIDUAL USED FOR THE SAME

TECHNICAL FIELD

The present invention relates to a method of authenticating individuals and an apparatus of authenticating individuals used for the same using eyeground image information, such as an eyeground blood vessel image and an eyeground blood flow map, and line-of-sight information. In further detail, the present invention relates to a method of authenticating individuals and an apparatus of authenticating individuals used for the same using the fact that an image range captured into the authentication apparatus is defined by a direction of a line of sight to analyze the direction of the line of sight and a moving route and check the result against personal data registered in advance.

BACKGROUND ART

In identity (individual) authentication, a scheme with fingerprints has been available from long ago, but, in recent years, in place of comparison by a visual check, various automatic authentication techniques in combination an image sensor or a semiconductor sensor and image processing by a computer have been developed and widely used. Also, a method has been put into commercial use in which the pattern of a fingertip and subcutaneous veins of a palm is read by using near-infrared light and an image sensor and to extract a feature, such as a branching point, for individual authentication. However, every method is not perfect yet, and the fight against forgery continues.

For example, Patent Documents 1 and 2 disclose clear, high-resolution fingerprint sensors using a laser, but these cannot determine simulated fingerprints. By contrast, Patent Document 3 discloses a method of performing individual authentication with a vein pattern by using an ordinary light beam and also determining whether a person to be authenticated is alive by optical detection of a pulse. Although this is not fingerprint recognition, it is also possible to confirm that the person to be authenticated is alive, and therefore this is effective at preventing forgery. However, there are problems, such as those as to reliability of authentication with a vein pattern and complexity of the apparatus.

On the other hand, when a laser is radiated toward a living body, an intensity distribution of its reflected scattering light forms dynamic laser speckles (a random granular pattern) with moving scattering particles, such as blood cells. It is known that this pattern is detected by an image sensor on an imaging plane and changes with time of the pattern at each pixel are quantified and displayed in a map, thereby imaging a blood flow distribution of capillary blood vessels near the surface of the living body. And, several technologies and apparatuses using this phenomenon to measure a blood flow map under the skin or of the eyeground have been suggested by the inventors (for example, refer to Patent Documents 4 to 9).

The inventors have formed a conception of using a blood flow map for individual authentication in connection with a fingerprint pattern, diligently proceeded studies, and already suggested an individual authentication method and its means by measuring a subcutaneous blood flow. That is, the inventors have suggested the individual authentication method including: (1) a step of enlarging a laser luminous flux for radiation to the pad of the finger tip and, with light reflected from a blood vessel layer under the skin, forming an image on an image sensor by using an optical system as laser speckles; (2) a step of finding an amount representing a velocity of time changes of a light-receiving amount at each pixel of laser speckles, for example, an average time change rate or an inverse of a degree of variations of the light-receiving amount integrated according to an exposure time of the image sensor, and obtaining a blood flow map of the pad of the finger tip by taking the found numerical value as a two-dimensional map; and (3) a step of comparing and determining a finger patter appearing as a blood flow map with personal data registered in advance, and an apparatus for executing each step (refer to Patent Document 10). Also, the inventors have improved the method described above and also suggested a method and means of using a laser having a specific wavelength as illumination light for radiation to a finger tip or radiating a plurality of lasers having different wavelengths simultaneously or sequentially to the finger tip to find superposing or a plurality of blood flow velocity maps with respect to reflected light (refer to Patent Document 11).

On the other hand, conventionally, a method and apparatus of coding/encoding eyeground information from an eyeground camera shot image to form signature data and a password has also been suggested (for example, Patent Documents 12 to 15). And, the inventors have created a very powerful individual authentication technique using the laser-speckle technology described above and eyeground information to use blood flow data, which is extremely difficult to forge, such as a run of blood vessels on a retina obtained by imaging an eyeground blood flow distribution, a distribution shape of arteries and veins and, furthermore, a distribution of a choroid blood vessel layer behind the retina and used blood flow data such as blood flow changes with time, and filed a patent application (refer to Patent Document 16).

[Patent Document 1] Japanese Unexamined Patent Application Publication No. 5-73666
[Patent Document 2] Japanese Unexamined Patent Application Publication No. 8-16752
[Patent Document 3] Japanese Unexamined Patent Application Publication No. 2003-331268
[Patent Document 4] Japanese Examined Patent Publication No. 5-28133
[Patent Document 5] Japanese Examined Patent Publication No. 5-28134
[Patent Document 6] Japanese Unexamined Patent Application Publication No. 4-242628
[Patent Document 7] Japanese Unexamined Patent Application Publication No. 8-112262
[Patent Document 8] Japanese Unexamined Patent Application Publication No. 2003-164431
[Patent Document 9] Japanese Unexamined Patent Application Publication No. 2003-180641
[Patent Document 10] International Publication No. 05/122896 Pamphlet
[Patent Document 11] International Publication No. 07/097129 Pamphlet
[Patent Document 12] Japanese Unexamined Patent Application Publication No. 7-213511
[Patent Document 13] Japanese Unexamined Patent Application Publication No. 11-215119
[Patent Document 14] Japanese Unexamined Patent Application Publication No. 11-149453
[Patent Document 15] Japanese Unexamined Patent Application Publication No. 2007-41831

[Patent Document 16] International Publication No. 07/142055 Pamphlet

DISCLOSURE OF THE INVENTION

Problems to be Solved by the Invention

It is said that every blood vessel pattern of the eye's retina differs depending on the individual and hardly changes its shape. Also, the blood flow distribution image and its changes with time can be considered as the most effective way of certifying identity and eliminating other persons. However, if the cream of cutting-edge micromachining technology is assembled, it is not definitely sure that fabricating a simulated eye with a passage mimicking a human retina blood flow is absolutely impossible. Moreover, eyeground blood flow information may be in danger of being stolen from a medical institution by a person plotting an intrusion. For example, if a person always using an eyeground blood flow authentication apparatus and therefore skilled in handling the apparatus fabricates a simulated eye mimicking the eyeground of another person and causes the apparatus to read it, the skilled person may be able to disguise himself or herself as the other person. That is, although the individual authentication apparatus based on imaging of the eyeground blood flow distribution previously suggested by the inventors is extremely strong, it is still difficult to say that the current one is perfect as it is. Therefore, an object of the present invention is to provide an improved technology for further reinforcing the individual authentication method using measurement of an eyeground blood flow distribution.

Means for Solving the Problems

In measuring an eyeground blood vessel or a blood flow distribution, with a change of the line of sight, the eyeball rotates and, when viewed from an apparatus for measuring an eyeground blood vessel or a blood flow distribution (individual authentication apparatus) side, it seems that the retina blood vessel pattern moves within an observation field of view. In other words, unless the line of sight of the subject eye coincides with the direction of the line of sight registered in advance, the individual authentication apparatus side recognizes the pattern as another pattern, rejecting as another person. Based on this principle, the present invention uses a property in which the line of sight of the subject and the observation field of view of a ground blood vessel image or a blood flow image have a one-to-one correspondence.

The object of the present invention described above is achieved by the following inventions recited in claims 1 to 5, based on the technical findings of the inventors described above.

The invention recited in claim 1 of the present invention is directed to an individual authentication method, wherein at least one information out of an eyeground blood vessel image information obtained by an optical means, eyeground blood flow distribution image information obtained by using a laser, and information relating to the change over time thereof is compared and collated with personal information registered in advance, the method comprising comparing and collating at least the one information out of the eyeground blood vessel image information, the eyeground blood flow distribution image information, and the information relating to the change over time thereof within a measurement field of view obtained in a direction of a line of sight fixed by a fixation index registered in advance with the personal information registered in advance.

The invention recited in claim 2 is directed to the individual authentication method according to claim 1, wherein the fixation index for fixing the direction of the line of sight has a plurality of fixation point candidates, and has an information of which of them to fixedly view registered in advance. In this invention of claim 2, it is intended that a plurality of fixation point candidates are prepared in an authentication apparatus, and a blood vessel pattern or a blood flow map obtained by the subject gazing a fixation point specified at the time of registration is compared and collated with the one at the time of registration, thereby eliminating other persons who do not know the fixation position at the time of registration.

The invention recited in claim 3 is directed to the individual authentication method according to claim 2, wherein the fixation points use a part of a character string, a part of a still image, or a part of a moving picture.

And, the invention recited in claim 4 relates to an individual authentication apparatus for use in the authentication method described above. That is, the invention relates to the individual authentication apparatus, wherein at least one information out of an eyeground blood vessel image information obtained by an optical means, eyeground blood flow distribution image information obtained by using a laser, and information relating to the change over time thereof is compared and collated with personal information registered in advance, the apparatus comprising means for fixing a direction of a line of sight.

The invention recited in claim 5 is directed to the individual authentication apparatus according to claim 4, wherein the means for fixing the direction of the line of sight includes a fixation index having a plurality of fixation point candidates.

Effects of the Invention

The eyeground blood vessel pattern and the eyeground blood flow distribution are congenital, regarded as hardware including extremely complex information, and can be used for individual authentication with accuracy much higher than that with fingerprints or the like. However, since the forging capability on a side disguising himself or herself as another person and plotting an intrusion always advances, it can be said that countermeasures are required endlessly. For example, although a method of identifying a forged eye by using a line of sight has already been suggested (for example, refer to Patent Document 15), the accuracy is low as long as corneal reflex or the like is used, and there is a danger of stealing with a hidden camera or the like. By contrast, since an optical system for observing an eyeground blood vessel pattern or a blood flow distribution is required to be used as being close to the eye, there is no space for mounting a hidden camera or the like. Also, when the face moves during observation, an error occurs in the conventional scheme of detecting a line of sight using corneal reflex, and a sufficient accuracy cannot be obtained. By contrast, in the optical system for observing an eyeground blood vessel pattern or a blood flow distribution, owing to the optical structure unique to the eyeball, the same place of the eyeground is captured within the observation field of view unless the line of sight is changed. The present invention uses this property, that is, the property of correctly determining the field of view captured by the eyeground observation system with the direction of the line of sight of the subject eye. Therefore, individual authentication method and apparatus with high accuracy and extremely superb in anti-forgery capability are provided.

Also, in the present invention, an authentication effect is increased by introducing means and techniques listed below. Firstly, a plurality of fixation point candidates are prepared in an authentication apparatus, and a blood vessel pattern or a blood flow map obtained by the subject gazing a fixation point specified at the time of registration is compared with or checked against the one at the time of registration, thereby eliminating other persons who do not know the fixation position at the time of registration. Even if a simulated eye mimicking an eyeground blood vessel with micromachining technology, the eye does not have a function of the retina in itself, and therefore it is impossible to gaze a specific direction.

Furthermore, even if the technology on an intrusion-plotting side improves and, for example, an image sensor is integrated at the back of a retina blood vessel for tampering so that an image viewed ahead of the line of sight can be extracted, by using a part of a general image, such as a character string, a still image, or a moving picture, as the plurality of fixation point candidates, where and how to gaze cannot be known by persons other than the relevant person. In the present invention, by using effectively the visual function of the eyes and combining with an acquired software element, that is, an intellectual information processing capability of the relevant person acquired through learning and memorization, an improvement is made to a stronger authentication system.

BRIEF DESCRIPTION OF THE DRAWINGS

FIG. 4 An example when a character string for a prompt for a computation process and hexadecimal digits as a fixation point are displayed on the fixation screen.

BEST MODE FOR CARRYING OUT THE INVENTION

Figure 1:
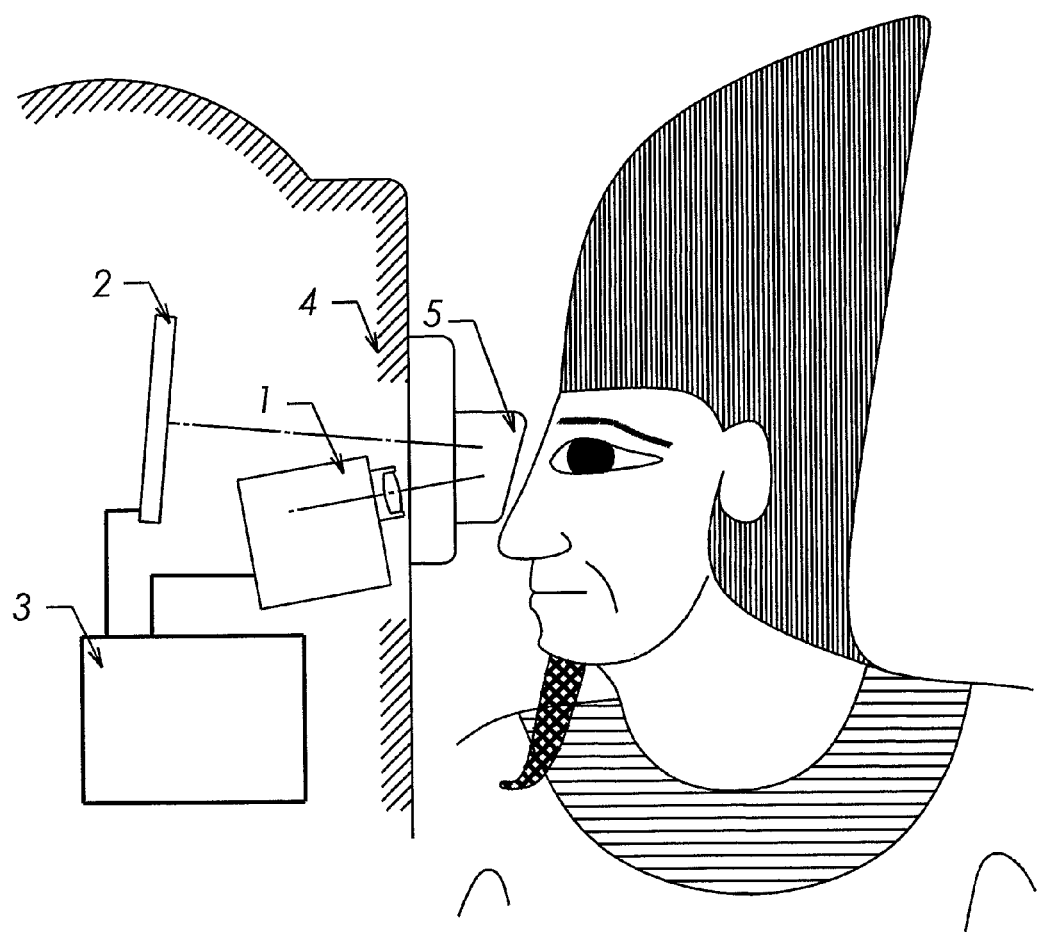
FIG. 1 A diagram for describing an individual authentication method using an eyeground blood vessel pattern or an eyeground blood flow distribution measurement.

The present invention is directed to an individual authentication method, wherein by using at least one of an eyeground blood vessel image information obtained by an optical technique, and eyeground blood flow distribution image information or information about changes with time thereof obtained by using a laser, this information is compared with and checked against personal information registered in advance, and wherein at least the one of the eyeground blood vessel image information, the eyeground blood flow distribution image information or information about changes with time thereof within a measurement eyesight obtained in a direction of a line of sight fixed by a fixation target registered in advance is compared with and checked against the personal information registered in advance.

The present invention uses either of two types of eyeground images: eyeground blood vessel image information obtained by an optical technique and eyeground blood flow distribution image information or information about changes with time thereof obtained by using a laser. The former represents a blood vessel pattern captured by a general eyeground observing optical system, such as an retinal camera. This is a technology roughly completed already, illuminating the eyeground with incoherent light, such as white light, to allow a blood vessel image to be captured by an image pickup element into a computer. When the subject moves the line of sight, the eyeball rotates, and the blood vessel pattern moves within a measurement field of view. Thus, by comparing and checking this line of sight and its movement information with and against a series of images registered in advance, it is possible to determine whether the identity is true. An image obtained with this method originally presents an image of a gray-scale blood vessel pattern and, immediately after simple image processing, such as contrast enhancement and outline extraction, it can be used as an image for authentication. However, due to simple pre-processing, it may not be impossible to create a simulated eye having a gray-scale image mimicking an eyeground blood vessel network pasted onto an eyeground portion and to cause a detection side to read for erroneous authentication.

The latter technology regarding an eyeground blood flow distribution uses a moving picture of an eyeground blood flow distribution captured by an eyeground blood flow imaging apparatus developed by the inventors and information about changes with time thereof. This is a new technology recently attaining a practical level. By illuminating a wide region of the eyeground with a laser and analyzing changes with time of a random interference pattern formed of scattering light on an image surface of the eyeground, a moving picture of a two-dimensional blood flow map is obtained. Due to complexity of a process of developing a blood flow map from a random granular pattern, this method requires longer analyzing time and higher cost. Moreover, unless a narrow channel equivalent to the eyeground blood vessel network is formed and scattering particles are actually let flow therethrough, a blood flow pattern does not appear. Therefore, it is extremely hard to forge. In the present invention, when these two eyeground images are used for individual authentication, in order to overcome a drawback for the former and construct a further stronger authentication system for the latter, line-of-sight information registered in advance in person is referred to in the course of authentication.

As described above, the eyeground blood vessel image information obtained by an optical technique or the eyeground blood flow distribution image information or information about changes with time thereof obtained by using a laser can be obtained with a known method/means. In the present invention, to obtain these pieces of information, information about the inside of a measurement field of view in a direction of a line of sight fixed with a fixation target registered in advance.

For example, eyeground blood flow imaging apparatuses have been developed originally as medical equipment, and have a function of, for a patient with unstable fixation, analyzing in which direction and how match the subject eye moves and shifting a blood flow map according to a movement vector for superposition. Here, since resolution with respect to the movement of fixation is normally on the order of 0.1 degree, even a slight movement of fixation can also be detected. In other words, at the time of imaging an eyeground blood flow, information about the movement of fixation has been grasped already with high accuracy. On the other hand, by adapting a condition registered in advance in person to a certain moving image, theoretical fixation movement information can be defined. By comparing and checking this theoretically found tracking information and an azimuth of fixation actually obtained from the subject eye and changes with time thereof with each other, it can be determined whether the identity is true.

The human image processing function is extremely superb, including, for example, a capability of extracting the outline of a known pattern buried in a random pattern and a stereopsis capability using parallax between the eyes. Thus, by using these, the line of sight can also be defined in a specific direction.

In the present invention, preferably, a fixation target is preferably used to fix the direction of the line of sight, the fixation target has a plurality of fixation point candidates, and has information of which of them to fixedly view registered in advance. And, as fixation points, a part of a character string, a part of a still image, or a part of a moving picture is preferably used. When the fixation target represents an image or character/number display screen, by designating, with the line of sight, an intellectual work result registered in advance, such as one that can be thought from the displayed image or character, a computation result, or a translation or conversion result, other persons who do not know the procedure can be eliminated. When a still image is used as a fixation screen, the order of viewing a plurality of fixation points and a fixation time for each can be detected and, for example, be compared with information, such as that indicative of five seconds or longer or within three seconds. Also, when a moving picture is used as a fixation target, an azimuth of fixation and changes with time thereof can be detected, and be compared with information registered in advance.

Specifically, for example, even if only a date, a time, and a numerical string can be viewed in line in the authentication apparatus, which computation procedure is used for these numerical character strings can be freely determined by the relevant person, and simple encoding can also be made. If the relevant person has registered "sequentially view numbers of two digits obtained by summing the numbers representing the time and then adding 3 thereto", it can be said that it is extremely difficult for another person to estimate such a computation result and send an instruction to a simulated eye so that it is controlled to fixedly view a predetermined location quickly.

Also, when a part of the moving image described above is used as a fixed point, it is possible to register in advance which to fixedly view and use, for determination of identify authentication, the state in which a measurement field of view of an eyeground image or an eyeground blood flow image moves according to the movement of a fixation target within the moving picture, that is, whether the result obtained by analyzing the azimuth of the line of sight and changes with time thereof coincides with the registered movement information of the fixation target.

The individual authentication method of the present invention as described above can be implemented by using an apparatus described below. That is, the apparatus is an individual authentication apparatus, wherein by using at least one of an eyeground blood vessel image information obtained by an optical technique, and eyeground blood flow distribution image information or information about changes with time thereof obtained by using a laser, this information is compared and collated with personal information registered in advance, wherein means for fixing a direction of a line of sight is provided. As the means for fixing the line of sight, means including a fixation target. And, in this apparatus, the means for fixing the direction of the line of sight preferably includes a fixation target having a plurality of fixation point candidates.

In the following, the principle of the present invention is described by using the drawings. In FIG. 1, 1 denotes an eyeground blood flow imaging apparatus or an eyeground image pickup apparatus, 2 denotes a fixation screen, 3 denotes authentication-purpose information processing apparatus, 4 denotes a barrier wall separating the inside and outside of an authentication system, and 5 denotes a hood that blocks surrounding light for easy observation of the eyeground. When a human outside of the authentication system focuses his or her eye on a predetermined position inside the hood, the eyeground blood flow imaging apparatus or eyeground image pickup apparatus 1 in FIG. 1 starts operation to cause data to be sent to the authentication-purpose information processing apparatus 3. If the subject fixedly views the predetermined position in the fixation screen 2 according to the details registered in advance, a blood flow image or blood vessel image data obtained by the eyeground image pickup apparatus 1 is compared with or checked against a registered image inside the authentication-purpose information processing apparatus 3 for determination whether the identity is true.

Figure 2:
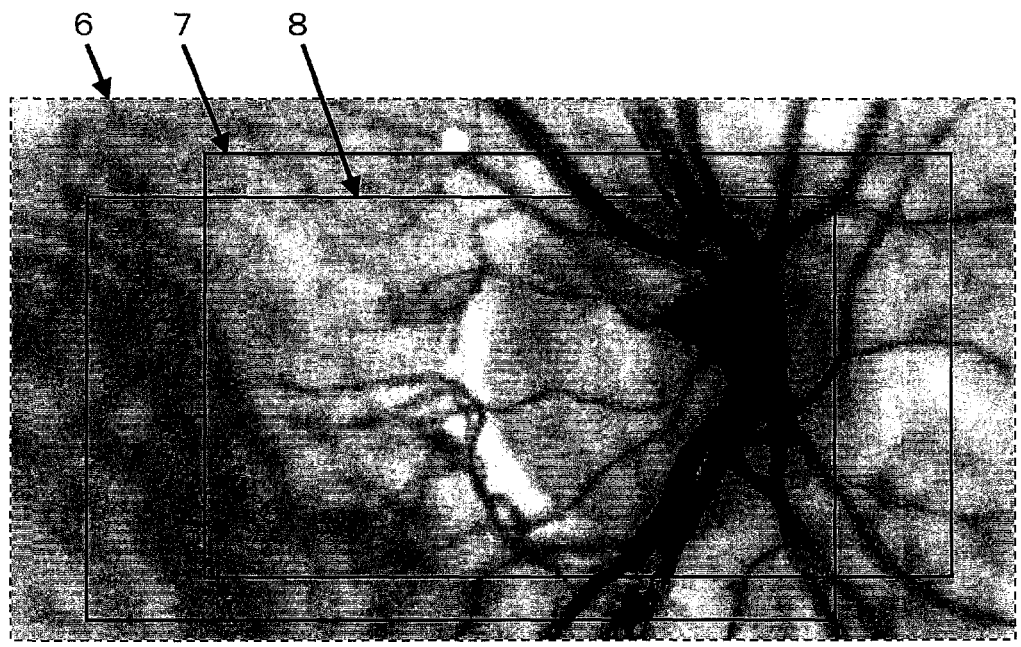
FIG. 2 A diagram for describing an example of a difference between an entire image of an eyeground blood flow image or an eyeground blood vessel image and an image obtained when a fixation position is changed.
Figure 3:
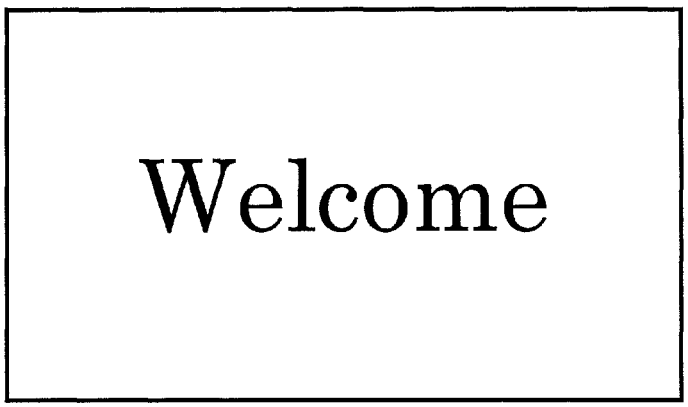
FIG. 3 An example when a character string is used as a fixation screen.

6 in FIG. 2 denotes an entire image of the eyeground blood flow image or the eyeground blood vessel image, and FIG. 3 depicts an example where a character string is used as a fixation screen. The eyeground blood flow image or the eyeground blood vessel image actually captured into the authentication system is within a limited region, such as within a frame denoted as 7 or 8 in FIG. 2. For example, although the fixation image of FIG. 3 uses a common word, when the subject fixedly views the head character W, the eyeground blood flow image or the eyeground blood vessel image captured correspondingly within an observation field of view is such denoted as 7 in FIG. 2. By contrast, when the subject fixedly views the second character e, a portion denoted as 8 of FIG. 2 is captured. This shift of the map is significant, and has a sufficient capability of discriminating between the relevant person and another person.

Figure 4:
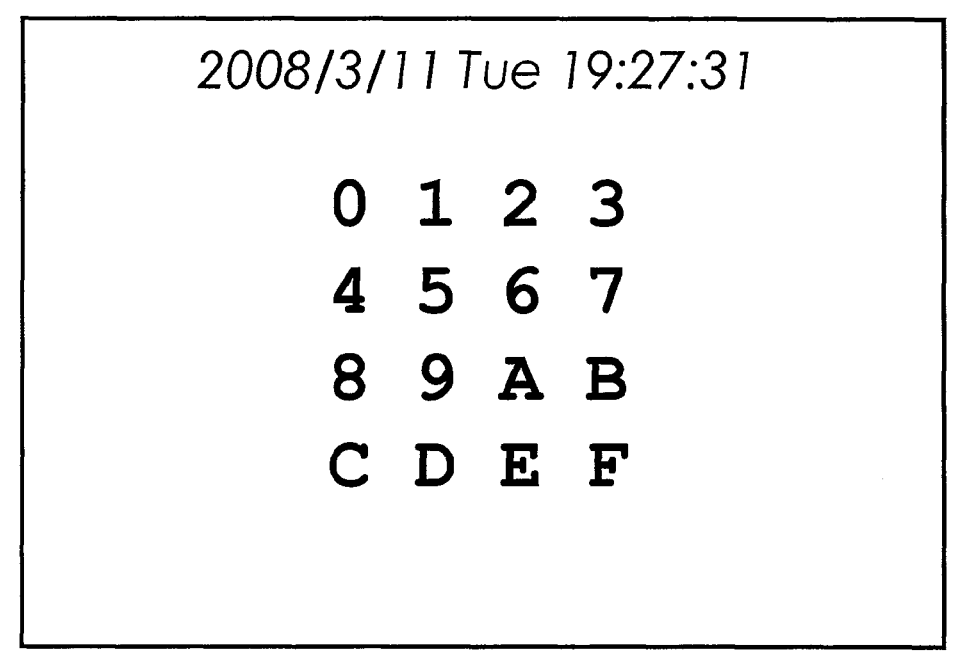

Also, FIG. 4 depicts an example in which character information for a prompt for a computation process and hexadecimal digits as a fixation point are displayed on the fixation screen. For such a screen, various processes can be thought. For example, with Tuesday as the third day of the week and March, 11, a person can be set to use 3+3+11=17 and fixedly view 7, which is the first digit number of the answer. Another person may convert 17 to a hexadecimal number and fixedly view 1, which is the first digit number. When a time display when detection starts is 31 seconds and there is enough time until switching, the numbers representing 27 minutes can be reversed for registration in a manner such that 7 is fixedly viewed for three seconds or more and then 2 is fixedly viewed for one second or more. The registered details at this time have such representation as "fixedly view the lower digit of the number representing the minutes for three seconds or more and the upper digit for one second or more". In this manner, if the time for gazing each fixation point is also registered in advance, it can be used for individual authentication.

As an example of the case where animation is used for a fixation screen, for example, it is assumed to display a screen having flowers of various types and several flying butterflies varied in color with each butterfly's color changing with time among seven colors. In such an example, an extremely elaborate registration is possible, such that "by taking anywhere as a starting point, firstly view a blue butterfly; when it changes to another color, view a yellow butterfly; and when it further changes to another color, view a tulip".

Also, if a function is provided such that the moving picture does not start if the eyeground blood vessel image or the eyeground blood flow image does not coincide with the one registered at the registered first fixation point, the details of the moving picture can be prevented from being disclosed to intruders, and therefore it can be said as being safer.

In a general authentication apparatus, before biometric authentication starts, the ID of the subject is often first entered with a card, a registration number, or the like. Although the image for use in fixation, such as the one depicted in FIG. 4, may be used commonly for all registered members, if a stronger authentication system is desired to be made, an original image uniquely created by himself or herself can be registered and read according to the ID.

It is possible to register separate images and logics for the right eye and the left eye for use by switching between normal use and emergency use.

Although the eyeground blood vessel network represents an extremely sophisticated pattern to identify each person, it is no wonder that a person may put micromachining technology to full use to try to artificially reproduce this pattern. However, like the present invention, a technology of instantaneously determining which position of the moving image created by another person and moving the forged eye toward the position for tracking is considered as being extremely difficult.

INDUSTRIAL APPLICABILITY

An individual authentication system according to the present invention combines image information obtained by an eyeground blood vessel shooting apparatus or an eyeground blood flow distribution moving imaging apparatus, and fixation point information known only to the relevant person. Among those of the former, the technique of shooting an eyeground blood vessel has been present from long ago and, with a simple gray-scale image, forgery is relatively easy. However, if this technology is combined with the latter fixation point information, an extremely powerful individual authentication system can be configured. Furthermore, among those of the former, the apparatus imaging an eyeground blood flow distribution as a moving picture is based on the technology recently developed by the inventors, in which no signal can be obtained unless a fine flow path mimicking a blood vessel network is artificially created and scattering particles are actually let flow, and therefore forgery is extremely difficult. If this is combined with the latter fixation point information, an ultimate individual authentication system can be constructed in which the image processing capability of the human eyes, memorization of the brain, and computation processing capability are fully used. Whether to use the eyeground blood vessel image or to use the eyeground blood flow image can be appropriately determined in consideration of authentication accuracy required, use condition, confidential details, management cost, and others. By fully using these advantages, the present invention can be used for security management at various levels, such as monitoring of the comings to and goings from an important facility for which break-in of outsiders should be prevented, immigration management, and acquirement of a right to access to a highly-confidential information system.

The invention claimed is:

1. A method of authenticating an individual, wherein at least one information out of an eyeground blood vessel image information obtained by an optical means, eyeground blood flow distribution image information obtained by using a laser, and information relating to the change over time thereof is compared and collated with personal information registered in advance, the method comprising:
providing a fixation screen displaying a fixation target having a plurality of fixation point candidates for fixing the direction of the line of sight, said plurality of fixation point candidates being simultaneously displayed to the individual,
registering in advance one of the fixation point candidates to fixedly view on the fixation screen, and
comparing and collating at least the one information out of the eyeground blood vessel image information, the eyeground blood flow distribution image information, and the information relating to the change over time thereof within a measurement field of view obtained in a direction of a line of sight registered in advance with the personal information registered in advance.

2. The method of authenticating an individual according to claim 1, wherein the fixation points use a part of a character string, a part of a still image, or a part of a moving picture.

3. An apparatus of authenticating an individual, wherein at least one information out of an eyeground blood vessel image information obtained by an optical means, eyeground blood flow distribution image information obtained by using a laser, and information relating to the change over time thereof is compared and collated with personal information registered in advance, the apparatus comprising:
an image pickup apparatus for obtaining a blood flow image or blood vessel image data as the one information;
a fixation screen displaying a fixation target having a plurality of fixation point candidates for fixing a direction of a line of sight, said fixation screen displaying said plurality of fixation point candidates simultaneously to the individual; and
an authentication-purpose information processing apparatus being connected with both of the image pickup apparatus and the fixation screen for registering in advance one of the fixation point candidates to fixedly view on the fixation screen, wherein the blood flow image or blood vessel image data obtained by the image pickup apparatus when a subject fixedly views one of the fixation point candidates registered in advance on the fixation screen is compared and collated with the personal information registered in advance in the authentication-purpose information processing apparatus.

4. The method of authenticating an individual according to claim 1, wherein:
the personal information registered in advance corresponds to a desired line of sight;
said comparing and collating determines if the eye information from the measurement field of view obtained in the direction of the line of sight registered in advance corresponds to the desired line of sight in the personal information in order to authenticate an individual.

5. An apparatus in accordance with claim 3, wherein:
the personal information registered in advance corresponds to a desired line of sight;
said authentication-purpose information processing apparatus determines if the eye information from the measurement field of view obtained in the direction of the line of sight registered in advance corresponds to the desired line of sight in the personal information in order to authenticate an individual.

6. A method of authenticating an unknown individual with a known individual, the method comprising:
determining eye blood vessel information for the known individual, the eye blood vessel information corresponding to a desired orientation of the eye of the known individual;
simultaneously providing a plurality of fixation points to an eye of the unknown individual, each of said plurality of fixation points providing a separate orientation of the eye and when viewed by the eye of the unknown individual, one of said fixation points being a desired fixation point arranged to position the eye of the unknown individual in the desired orientation;

instructing the unknown individual to view the desired fixation point with the eye;

measuring eye blood vessel information for the unknown individual while the unknown individual is to be viewing the desired fixation point with the eye;

comparing the eye blood vessel information from the known and unknown individual to determine if the eye blood vessel information for the unknown individual corresponds to the eye blood vessel information for the known individual, said comparing also determining if the measured eye blood vessel information for the unknown individual corresponds to the desired orientation of the eye;

authenticating the unknown individual as the known individual if the eye blood vessel information of the unknown individual corresponds to the known individual, and if the measured eye blood vessel information for the unknown individual corresponds to the desired orientation of the eye.

7. A method in accordance with claim 6, wherein:
each of the plurality of fixation points are selectively and individually viewable by the eye of the unknown individual when displayed simultaneously;
the eye blood vessel information of the known user is unique to the desired orientation of the eye.

8. A method in accordance with claim 6, wherein:
the eye blood vessel information includes one of eyeground blood vessel image information obtained by an optical means, eyeground blood flow distribution image information obtained by using a laser, and information relating to a change over time thereof.

9. A method in accordance with claim 6, further comprising:
providing a fixation screen displaying a fixation target having the plurality of fixation points, each of the plurality of fixation points being arranged for fixing a separate direction of a line of sight of the eye.

10. A method in accordance with claim 7, wherein:
the eye blood vessel information includes one of eyeground blood vessel image information obtained by an optical means, eyeground blood flow distribution image information obtained by using a laser, and information relating to a change over time thereof;
a fixation screen is provided for displaying a fixation target having the plurality of fixation points, each of the plurality of fixation points being arranged for fixing a separate direction of a line of sight of the eye.

11. A method in accordance with claim 6, wherein:
said determining of eye blood vessel information includes separate eye blood vessel information for each of a plurality of desired orientations of the eye;
said plurality of fixation points includes a plurality of desired fixation points, each of said plurality of desired fixation points being arranged to position the eye of the unknown individual in one of the plurality of desired orientations of the eye;
the unknown individual is further instructed to view another one of the plurality of desired fixation points;
further eye blood vessel information is measured for the unknown individual while the unknown individual is to be viewing the another desired fixation point with the eye;
said comparing also determines if the measured further eye blood vessel information for the unknown individual corresponds to the desired orientation of the eye corresponding to the another desired fixation point;
further authenticating the unknown individual as the known individual if the measured further eye blood vessel information for the unknown individual corresponds to the desired orientation of the eye corresponding to the another desired fixation point.

12. A method in accordance with claim 6, wherein:
information is displayed to the unknown individual during said providing of the plurality of fixation points;
said instructing of the unknown individual includes using the information displayed with the plurality of fixation points to determine the desired fixation point.

* * * * *